United States Patent [19]

Bertland et al.

[11] Patent Number: 4,540,669
[45] Date of Patent: * Sep. 10, 1985

[54] HERPES SIMPLEX TYPE I SUBUNIT VACCINE

[75] Inventors: Alexander U. Bertland, Lansdale; George P. Lampson, Hatfield, both of Pa.

[73] Assignee: Merck & Co., Inc., Rahway, N.J.

[*] Notice: The portion of the term of this patent subsequent to Mar. 2, 1999 has been disclaimed.

[21] Appl. No.: 285,162

[22] Filed: Jul. 23, 1981

Related U.S. Application Data

[63] Continuation-in-part of Ser. No. 186,365, Sep. 11, 1980, Pat. No. 4,317,811.

[51] Int. Cl.$^3$ .............................................. A61K 39/245
[52] U.S. Cl. ........................................ 435/235; 424/89
[58] Field of Search .................. 424/89; 435/235, 239

[56] References Cited

U.S. PATENT DOCUMENTS 4,317,811 3/1982 Bertland et al. ...................... 424/89

FOREIGN PATENT DOCUMENTS 0089854 9/1983 European Pat. Off. ............... 424/89
WO83/02897 9/1983 PCT Int'l. Appl. ................... 424/89

OTHER PUBLICATIONS

Thomson et al., Infection & Immunity 41 (2): 556–562, Aug. 1983 Comparison of Effects of Adjuvants on Efficacy of Virion Envelope Herpes Simplex Virus Vaccine of Mice.
Allen et al., J. Inf. Dis. 145 (3): 413–420, Mar. 1982, Concept Review of Genital Herpes Vaccines.
Slichtova et al., Arch. Virol. 71:75–78 (1982) Immunogenicity of a Subviral Herpes Simplex Type I Preparation: Reduction of Recurrent Disease in Mice.
Hilfenhaus et al., Behring Inst. Mitt. No. 69: 45–56 (1981) Prospects for a Subunit Vaccine Against Herpes Simplex Virus Infections.
Schneweis et al., Med. Microbiol. Immunol. 169: 269–279 (1981) The Influence of Different Modes of Immunization on the Experimental Genital Herpes Simplex Virus Inf. of Mice.
Hilfenhaus et al., Med. Microbiol. Immunol. 169: 225–235 (1981) Protectivity of Herpes Simplex Virus Antigens: Studies in Mice on the Adjuvant Effect etc.
Klein et al., Arch. Virol. 68: 73–80 (1981) Efficacy of a Virion Envelope Herpes Simplex Virus Vaccine Against Experimental Skin Infections in Hairless Mice.
Cappel et al., Arch. Virol. 65: 15–23 (1980) Efficacy of a Nucleic Acid-Free Herpetic Subunit Vaccine.
Kitces et al., Infect. & Immun. 16: 955–960 Jun. 1977, Protection from Oral Herpes Simplex Virus Infection by Nucleic Acid-Free Virus Vaccine.
Glorioso et al. C.A. 86: 87551c (1977) of J. Immunol. 118(1): 114–121 (1977).
Cohen et al. CA. 89:103367s (1978) of J. Virol. (1978) 27 (1): 172–181.
Vestergaard C.A. 88: 134680x (1978) of P.S.E.B.M. 1977: 349–353.
Eisenberg C.A. 91: 173200x (1979) of J. Virol. (1979) 31 (3): 608–620.
Vestergaard C.A. 90:184708z (1979) of Infect. Immun. (1979) 23(3):553–558.
Chen C.A. 90: 134184e (1979) Virology (1978) 91 (2): 234–242.
Vestergaard C.A. 93: 225621y (1980) of Ger. Offen. 2949031 Jul. 17, 1980.
Hilfenhaus C.A. 96: 168577z (1982) of Behring Inst. Mitt. 1981 69: 45–56.
Thomson C.A. 99: 86277z (1983) of Infect. Immun. 1983 41 (2): 556–562.
Larson C.A. 98: 149580v (1983) of U.S. No. 4,374,127, Feb. 15, 1983.
Skinner C.A. 99: 200489x (1983) of Eur. Pat. Appl. Ep No. 89854, Sep. 28, 1983.
C.A. 70: 17866e (1969), Sitnikov et al.
C.A. 90: 97989y (1979), Tumilowicz et al.
C.A. 90: 109,946x (1979), Shiraishi et al.
C.A. 76: 139079v (1972), Burbidge.

*Primary Examiner*—Shep K. Rose
*Attorney, Agent, or Firm*—Richard A. Elder; Donald J. Perrella; Hesna J. Pfeiffer

[57] ABSTRACT

A herpes simplex type I subunit vaccine is prepared from infected chick embryo cells by ultra extraction of the virus while the infected cells are still attached to the growth surface.

1 Claim, No Drawings

HERPES SIMPLEX TYPE I SUBUNIT VACCINE

This is a continuation in part of Application Ser. No. 186,365, filed Sept. 11, 1980, now U.S. Pat. No. 4,317,811, issued Mar. 2, 1982.

BACKGROUND OF THE INVENTION

1. Field of the Invention

This invention relates to the preparation of a herpesvirus subunit vaccine, and in particular to a Herpes simplex type 1 subunit vaccine.

Herpesviruses are ubiquitous in nature; natural hosts include the frog, chicken, mouse, guinea pig, cat, dog, swine, cow, horse, monkey and man. Man is the natural host for Herpes simplex type 1, varicella/zoster, cytomegalovirus and Epstein-Barr. Clinical illness caused by herpes viruses presents a significant health problem for which no effective preventive measures are available. Herpes simplex type 1 (HSV1) is transmitted by the oral-respiratory route and is most frequently associated with oral lesions.

Members of the herpesvirus group are relatively large enveloped ether-sensitive DNA viruses. Herpes simplex type 1 viruses have been shown characteristically to contain two predominant molecular weight groups of envelope gylcoproteins.

Herpesviruses present unique and individual problems for vaccine development, especially for use in man. Generally, viral vaccines, whether live attenuated vaccines or killed inactivated vaccines, are prepared from virus contained in animal host fluids or cell culture fluids or viral concentrates derived therefrom. However, herpesviruses in general tend to be more cell-associated than many other viruses, i.e., do not shed into the fluids, and, especialy some members of the group, do not propagate readily to the high level of virions required for large scale manufacture of vaccines. Additionally, certain herpesviruses are suspected of being oncogenic for man. Preparation of vaccines from such viruses presents a special problem in that the vaccine must be free of any viral genetic information capable of inducing cancer. Even inactivated whole virus vaccines are viewed as potentially hazardous in such cases because they contain viral nucleic acid. Recently, efforts toward inproved viral vaccines have lead to the development of subunit or "split" vaccines to reduce or remove unwanted host or viral components in the vaccines. An example in point is the preparation of influenza viral subunit vaccine from infected chick egg allantoic fluid to reduce the toxicity and pyrogenicity as described in U.S. Pat. No. 3,962,421. However, such subunit vaccines have not emphasized or demonstrated the removal and/or deactivation of viral genetic information as will be needed for viruses suspected of playing an etiologic role in cancer.

2. Objects of the Invention

It is an object of the present invention to provide a subunit antigen for a herpes simplex type 1 virus. Another object is to provide an immunogenic but non-pathogenic herpes simplex type 1 subunit antigen. A further object is to provide a herpes subunit antigen which can be used as a vaccine which protects a subject against the effects of this virus on both initial and subsequent challenge. Yet another object is to provide a method for effectively solubilizing and extracting nonpathogenic immunogenic antigens from virus-infected cells. Another object is to provide a method for concentrating these antigens and removing unwanted protein and nucleic acid. Another object is to provide compositions containing a herpes simplex type 1 subunit virus which are stable and storable. Still another object is to provide physiologically acceptable compositions for administering a herpes simplex type 1 subunit vaccine. These and other objects of the present invention will be apparent from the following description.

SUMMARY OF THE INVENTION

Primary chick embryo cells infected with HSV1 are prepared and subjected to the following sequence of operations to extract and concentrate the nonpathogenic, immunogenic antigens, separate them from unwanted materials, and treat them to render them satisfactory for use as a vaccine:

(1) the infected cells are extracted with urea while the cells are still attached to the growth surface, (2) the urea extract is purified, concentrated and inactivated, (3) the inactivated extract is treated to separate immunogenic fractions.

DETAILED DESCRIPTION

According to the present invention the starting material is herpes simplex virus type 1 (HSV1) infected cells propagated in cell culture. The cell may be any cell capable of being infected with HSV1 and of producing the desired viral antigens and considered acceptable for the preparation of a vaccine. For HSV1 vaccines for man, for example, a suitable cell culture system is primary chick embryo cells propagated as monolayers in roller bottles by procedures commonly used by those skilled in the art. The cells are infected with the HSV1 virus at a low multiplicity of infection (MOI, i.e., the number of virus particles per cell), such as an MOI of from about 0.001 to about 1.0, preferably about 0.01, by techniques commonly used by those skilled in the art and the cultures are incubated until viral cytopathogenic effect is observed in a large proportion of the cells, typically about 75% of the cells. At the end of the incubation period, the cell culture medium is removed and the cell monolayer is optionally washed with a salt solution, e.g. phosphate buffered saline (PBS).

HSV1 subunit antigens are then extracted directly from the cells attached to the growth surface by treating the cells with an aqueous urea solution, for example, a solution in PBS or water containing urea in concentration of at least about 2M, at elevated temperature for up to several hours. The urea concentration may be from about 2M to about 8M, preferably about 4M. The extraction preferably takes place with agitation. The elevated temperatures may be from about 30° C. to about 45° C. The extraction time may be from about 0.5 hour to about 5 hours. Either a single continuous or several successive extractions may be performed. Direct chemical extraction of the intact monolayer cell cultures offers a significant practical advantage for large scale vaccine manufacture as it does not require mechanical removal of the cells from the cell growth surface. It has also been found to give a higher protein yield by reducing physical losses involved in mechanical harvesting of cells. Under properly controlled conditions this procedure improves antigen purity by selective extraction of antigens.

The urea extract is then clarified, e.g., by centrifugation or filtration, and the supernatant liquid is then concentrated to reduce the volume of liquid. Preferably the volume is reduced to from 1/10 to 1/100 or more of the original volume. The concentrate is optionally but preferably homogenized and inactivated, e.g., by sonication or treatment with a detergent. Improved yields are obtained by heating the inactivated concentrate to from about 50° C. to about 75° C., e.g., by heating in a water bath.

The concentrate next is treated to remove DNA, e.g., by treating with an enzyme which degrades DNA, such as DNase to hydrolyze DNA, and fractionated chromatographically to separate immunogenic fractions. The immunogenic fractions are pooled and optionally but preferably homogenized and sterile filtered. The final product may be further treated by addition of formalin to a concentration of 90–100 μg/ml and by addition of thimerosal (1:20,000 vol/vol) to further insure against the presence of infectious viruses.

The herpes simplex type 1 immunogenic antigens of the present invention are immunogenic in mammalian species, e.g., mice, guinea pigs and baboons, and are useful as a vaccine in an immunologically effective amount to protect against herpes simplex type 1. The immunogenic antigens of the present invention may be administered by any convenient route, e.g. subcutaneously intraperitoneally, or intramuscularly, in the presence of a physiologically acceptable diluent, in a dosage range of from about 0.1 to about 100 μg/dose preferably from about 5 to about 50 μg/dose, in order to obtain the desired immunogenic effect. The antigens may be administered in a single dose or in a plurality of doses at intervals of several weeks or more.

The immunogenic antigens of the present invention may be administered, if desired, in combination with vaccine stabilizers and vaccine adjuvants. Typical stabilizers are, for example, sucrose, an alkali metal hydrogen phosphate salt, glutamate, serum albumin, gelatin, or casein. The stabilizer may be any one or more of the foregoing. The adjuvant may be, for example, alum or a composition containing a vegetable oil, isomannide monooleate and aluminum monostearate. The immunogenic antigens of the present invention may be stored under refrigeration or in frozen or lyophilized form.

The immunogenic antigen of the present invention contains about 5 or 6 bands having minimum molecular weight greater than 68,000 daltons as determined on SDS gel electrophoresis. The intact antigenic product has a molecular weight greater than $1 \times 10^6$ daltons as determined on Sephadex 6B-Cl gel electrophoresis. The antigenic product is substantially free of glycoprotein (no glycoprotein detected at 230 μg protein/gel) and of DNA (none detected at minimum sensitivity of 50 μg/ml). The antigenic product contains from about 0.1 to about 0.7 μg carbohydrate per 1 μg of protein, and contains one lipid band having a molecular weight between about 60,000 and about 70,000 daltons as determined by SDS gel electrophoresis.

The following examples illustrate the present invention without, however, limiting the same thereto. All temperatures are expressed in degrees Celsius.

EXAMPLE 1

A cell sheet of chick embryo cells grown in roller bottles is infected on the fourth day after planting with herpes simplex type 1 virus. Six days post infection the cells are washed with 30 ml of PBS per liter bottle. The virus is extracted from the cells by treating the cells with 4M urea in PBS for 75 minutes at 37° while rolling. The urea also may be made up in water. About 25 ml of the urea solution are used per liter bottle. The urea solution is sterilized prior to use by sterile filtering through a 0.22 μMillipore 293 mm filter. A second extraction under similar conditions is carried out and the two urea extracts are combined and clarified by centrifuging at 14,000× for 10 minutes with a continuous flow DeLaval centrifuge.

The supernatant liquid is concentrated 85-fold at room temperature on Amicon Model TCID stack filter units, consisting of five 150 mm XM-100 filter pads. This concentrate is further concentrated to a 450-fold final concentration at room temperature on a Amicon Model 2000 stirred filter unit using an SM-100 Amicon filter 150 mm, at room temperature. After concentration, the filter is rinsed with 20 ml of eluate, which then is added to the concentrate. Next the concentrate is sonicated for 3 minutes at 60% of maximum power with a high frequency probe sonicator (BIOSONIC II) in an ice bath. The sonicated material is heated in a 60° water bath for three hours, then cooled to room temperature.

The concentrate then is treated with DNase at a concentration of 10 μg/ml + 0.01M MgCl$_2$ for 3 hours at room temperature and overnight at 4°. The DNase treated concenterate then is loaded on a 10 cm × 100 cm Pharmacia column packed with B10-gel A-5M or Sephadex 6B-Cl and is gel chromatographed at room temperature. Fractionation is monitored by ultraviolet adsorption. The fractions at void volume are pooled and sonicated with a probe sonicator in an ice bath. The sonicated material then is filtered through a 0.45μ Gelman filter of appropriate size, to obtain a sterile product which is stored at 4° C. The final product is sterility tested in thioglycolate medium, one ml product per 15 ml medium, and incubated at 32° for 5 days.

The product is then examined for the presence of nucleic acid by a fluorometric method using ethidium bromide, Analytical Biochemistry 46, 135–145 (1972). Protein concentration of the product is determined by the Lowry method, Anal. Biochemistry 48, 422–427 (1972). Carbohydrates are quantitatively determined by the phenolsulfuric acid method, Anal. Biochemistry 28, 350 (1956). Lipid content is identified after SDS polyacrylamide gel elefctrophoresis by staining with Sudan Black, Bull. Soc. Chim. Biol. 51: 1367 (1969). SDS gel electrophoresis is also used for the determination of the number of minimum molecular weight peptides present in the final product with Coomassie Blue, Journal of Biological Chemistry 244, 4406 (1969). It is also tested for glycoprotein content using periodic acid-Schiff's stain, Methods in Enzymology XXXII, pp. 92–102, Academic Press. The product is further examined by both rocket immunoelectrophoresis and immunoelectrophoresis for the presence of chick cell protein, Manual for Quantitative Immunoelectrophoresis, ed. Axelson et al., Scand. Journal of Immunology 2 suppl. 1, 37–46 (1973) for rocket immunoelectrophoresis, and Immunoelectrophoresis (IEP), Hyland Diagnostics, Div. Travenol Laboratories, Inc. Deerfield, Ill. 60015 for immunoelectrophoresis, and quantitatively for any precipitating antigens using antibody prepared in rabbits. An electron microscopic record is made of the final product.

The product is optionally treated with formalin for 72 hours at 37° and with thimerosal (1:20,000). At the end of the formalin treatment excess formaldehyde is neutralized with NaHSO$_3$. A sterile suspension containing 30 ml PBS, 2 ml 10% NaPO$_4$ and 2.5 ml 10% alum is centrifuged at 3000×G. The supernatant liquid is decanted and 30 ml of product is added to the precipitate with stirring at room temperature for 2 hours. The absorbed product is centrifuged in a clinical centrifuge. The supernatant liquid is removed and the precipitate is resuspended to the original volume with phosphate buffered saline. The amount of protein adsorbed is determined by the amount of protein left unadsorbed in the supernatant liquid. The alum adsorbed product is stored at 4°.

EXAMPLE 2

Two groups of ICR/Ha mice, 20 mice per group, are injected intraperitoneally (i.p.) with two 0.5 ml injections on days 0 and 30 with either 0.5 ml injections on days 0 and 30 with either 0.5 ml of the alum adsorbed product of Example 1 or placebo. Each 0.5 ml dose of the alum adsorbed product of Example 1 contains 20 μg of HSV-1 subunit antigen. A third group of 5 mice receive no treatment. On day 44 the mice in all of the groups are challenged by infection with 0.5 ml of a $10^3$ dilution with HSV-1 (Schooler strain) i.p. and are monitored for survival for the next 21 days. Of the mice receiving the subunit antigen of Example 1, 19 (95%) are alive on day 65 while only 3 (15%) of the group receiving the placebo are alive. None of the group receiving no treatment is alive.

EXAMPLE 3

A group of 20 mice ranging in age from 3-12 weeks and ranging in weight from 20-35 g are injected intraperitoneally (i.p.) with two 0.5 ml doses of the alum-adsorbed product of Example 1 (20 μg/animal) at a one month interval. A second group of 20 mice receive a placebo and a third group of 37 mice receive no treatment. Two weeks after the last injection the mice are challenged with herpes simplex type 1, Schooler strain, (about $2\times10^5$ plaque formng units) by application to the abraded snout. Two mice from the placebo group die before challenge. Eighteen days post infection 17 mice (85%) are alive from the first group, and a combined total of 35 mice (64%) are alive from the 55 mice challenged from the placebo and no treatment groups.

We claim:

1. A herpes simplex type I immunogenic antigen having a molecular weight greater than $1\times10^6$ daltons and comprising about 5 or 6 bands having minimum molecular weight greater than 68,000 daltons, the antigen being substantially free of glycoprotein and of DNA, and containing from about 0.1 to about 0.7 μg carbohydrate per 1 μg of protein and containing one lipid band having a molecular weight between about 60,000 and about 70,000 daltons.

* * * * *